United States Patent
Panten et al.

(10) Patent No.: US 8,080,514 B2
(45) Date of Patent: Dec. 20, 2011

(54) 2-ALKOXYMETHYL-3-ISOALKENYL-1-METHYLCYCLOPENTENES, USE THEREOF, IN PARTICULAR AS FRAGRANCE SUBSTANCES, CORRESPONDING ARTICLES AND PRODUCTION METHODS

(75) Inventors: Johannes Panten, Höxter (DE); Horst Surburg, Holzminden (DE); Thomas Obrocki, Pattensen (DE); Erich Dilk, Holzminden (DE)

(73) Assignee: Symrise AG, Holzminden (DE)

( * ) Notice: Subject to any disclaimer, the term of this patent is extended or adjusted under 35 U.S.C. 154(b) by 732 days.

(21) Appl. No.: 12/248,168

(22) Filed: Oct. 9, 2008

(65) Prior Publication Data

US 2009/0092725 A1    Apr. 9, 2009

(30) Foreign Application Priority Data

Oct. 9, 2007  (EP) .................................. 07118101

(51) Int. Cl.
*A61Q 13/00*  (2006.01)
*C11B 9/00*  (2006.01)
*C07C 35/06*  (2006.01)

(52) U.S. Cl. ............................................ 512/8; 510/102
(58) Field of Classification Search ....... 512/8; 510/102
See application file for complete search history.

(56) References Cited

U.S. PATENT DOCUMENTS
4,795,738 A * 1/1989 Bedoukian ...................... 512/25
* cited by examiner

*Primary Examiner* — James J Seidleck
*Assistant Examiner* — Saira B Haider
(74) *Attorney, Agent, or Firm* — Connolly Bove Lodge & Hutz LLP

(57) ABSTRACT

Compounds of formula (A) are described

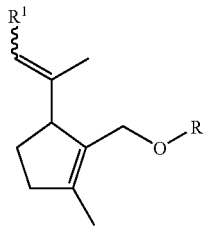

wherein, independently of one another, the following applies to groups R and $R^1$:
R is methyl or ethyl, and
$R^1$ is hydrogen or methyl, wherein the meandering line shows that for
$R^1$=methyl, the associated double bind is (E)- or (Z)-configured. Furthermore, methods for producing compounds of formula (A) and the use of corresponding compounds as fragrance and/or flavouring substances are described.

19 Claims, No Drawings

2-ALKOXYMETHYL-3-ISOALKENYL-1-METHYLCYCLOPENTENES, USE THEREOF, IN PARTICULAR AS FRAGRANCE SUBSTANCES, CORRESPONDING ARTICLES AND PRODUCTION METHODS

CROSS REFERENCE TO RELATED APPLICATION

This application claims benefit of priority to EP 07 118 101.0 filed on Oct. 9, 2007, which is incorporated herein by reference in its entirety.

The present invention relates to new compounds (2-alkoxymethyl-3-isoalkenyl-1-methylcyclopentenes) of a formula (A)

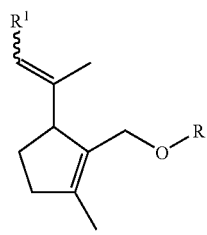

(A)

See below regarding the meaning of groups R and $R^1$. The present invention also relates to the use of new compounds as a fragrance and/or flavouring substance and as a means for increasing the odour of other fragrance substances perceived over a surfactant-containing aqueous solution, corresponding articles comprising one or more compounds according to the invention of formula (A), corresponding fragrance and flavouring substance compositions, corresponding methods for imparting, modifying and/or reinforcing an odour or taste, as well as corresponding production methods. Further aspects of the present invention emerge from the following description, the examples and the accompanying claims.

Despite a large number of already existing fragrance substances, there continues to be a general need in the perfume industry for new fragrance substances. In particular, there is a need for fragrance substances, which are distinguished by new original perfume notes and those, which have additional positive secondary properties going beyond their odour properties, such as, for example, a higher stability or yield under certain application conditions, better adhesion, very good blooming, a greater diffusivity or else a lower threshold value.

In particular, there is also a need for fragrance or flavouring substances with complex odour or taste properties, such as, for example, a combination of fruity, floral, sweet and osmanthus-like aspects which are in a position to produce in fragrance substance compositions, in particular perfume compositions or flavouring substance compositions, a combination of fruity (in particular apricot), floral (in particular lilac), sweet and osmanthus-like odour or taste notes. The present invention is therefore based on the object of disclosing fragrance and flavouring substances of this type.

According to the invention, this object is achieved by new compounds (2-alkoxymethyl-3-isoalkenyl-1-methylcyclopentenes) of formula (A) (see below)

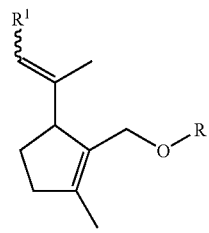

(A)

wherein independently of one another the following applies for groups R and $R^1$:
R is methyl or ethyl, and
$R^1$ is hydrogen or methyl, the meandering line indicating that for
$R^1$=methyl, the associated double bind is (E)- or (Z)-configured.

The present invention also relates to the corresponding use of compounds of formula (A) as a fragrance and/or flavouring substance, corresponding articles comprising one or more compounds of formula (A), in particular fragrance or flavouring substance compositions, (perfumed/flavoured) articles, which contain a sensorially effective quantity of one or more 2-alkoxymethyl-3-isoalkenyl-1-methylcyclopentenes, corresponding methods for imparting, modifying and/or reinforcing an odour or taste, production methods for the compounds of formula (A) according to the invention as well as production methods for articles according to the invention (in particular fragrance or flavouring substance compositions).

The invention is inter alia based on the surprising recognition that the 2-alkoxymethyl-3-isoalkenyl-1-methylcyclopentenes according to the invention of formula (A) are suitable as fragrance and flavouring substances.

Formula (A) comprises the following compounds:

compound 1a:

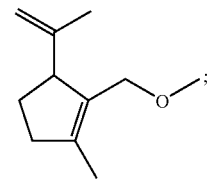

R = Me, $R^1$ = H compound 1b:

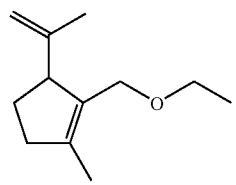

R = Et, $R^1$ = H compound 2a:

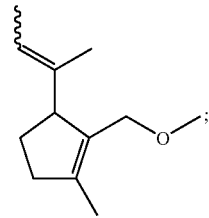

R = Me, $R^1$ = Me

-continued compound 2b:

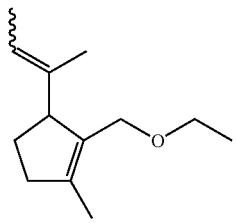

R =Et, R$^1$ = Me

The meandering line in the case of compounds 2a and 2b in this case shows that the associated double bind is either (E)- or (Z)-configured. The (E)-configured isomers of compound 2a or 2b will be designated 2aE or 2bE below, the (Z)-configured isomers will correspondingly be designed 2aZ or 2bZ.

The compounds 1a, 1b, 2aE, 2aZ, 2bE and 2bZ are novel.

In our own investigations, it has been found, in particular, that the compounds according to the invention of formula (A) are excellently suited for imparting, modifying and/or reinforcing the odour notes fruity (in particular apricot), floral (in particular lilac), sweet and osmanthus-like (osmanthus=complex, floral-fruity fragrance of *Osmanthus fragrans*). Individual odour descriptions are given in the following table:

| Compound/<br>Isomer mixture | Odour description |
| --- | --- |
| 1a | Fruity (apricot), sweet, osmanthus |
| 1b | Osmanthus-like, apricot, sweet, lilac, strong |
| 2aE/2aZ* | Strong osmanthus, fruity (apricot), sweet, floral |
| 2bE/2bZ* | Strong osmanthus, fruity (apricot), sweet, floral |

*in the (E)/(Z)-isomer mixtures, the (E)/(Z)-isomer ratio was 55:35.

Furthermore, for the compounds according to the invention of formula (A), in the tasting, the following taste properties were found: fruity, floral, sweet and osmanthus-like. It was also found that the compounds according to the invention of formula (A) are excellently suited for imparting, modifying and/or reinforcing the taste notes fruity (in particular apricot), floral (in particular lilac), sweet and osmanthus-like.

In contrast to the compounds according to the invention of formulas 2a or 2b, the compounds 3a or 3b surprisingly exhibit only a weak odour or taste.

3a

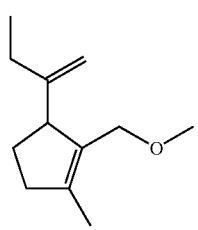

-continued

3b

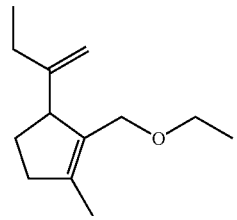

The compounds 3a or 3b are frequently present as secondary components in addition to the compounds according to the invention of formulas 2a or 2b. The compounds of formulas 3a or 3b, not according to the invention, may, however, be separated from the compounds of formulas 2a or 2b according to the invention by conventional separation methods, such as, for example distillation.

According to the invention, the compound of formula 1b (compound of formula (A) with R=ethyl and R$^1$=hydrogen) is particularly preferred. The compound of formula 1b is a compound with a particularly fruity (apricot), floral (lilac), sweet and osmanthus-like odour or taste note. A compound of formula 1b has a particularly expressive fruity (apricot), floral (lilac), sweet and osmanthus-like odour or taste, which is particularly surprising as (a) it differs structurally very clearly from known substances with the above-described odour properties and because (b) probably the structurally most similar known compound of formula 4b (see below) has no comparable odour.

The following Table 1 shows selected compounds, which substantially contribute to the sensory character of the osmanthus oil (*Osmanthus fragrans*) (source: G. Ohloff, *Riechstoffe und Geruchssinn*, page 164, Springer-Verlag, Berlin, 1990):

TABLE 1

| Structure | Odour properties |
| --- | --- |
| 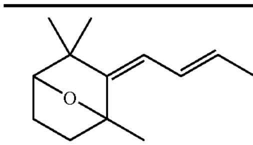 | Cassia buds, tomato blossom, exotic fruits |
| 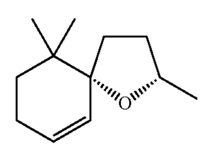 | Sensory principle of the tea flavour |
| 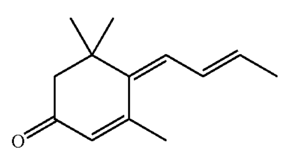 | Woody, balsamic, tabaco-like |

It can be seen that the compounds responsible for the sensory character of the osmanthus oil are clearly structurally different from the compounds of formula (A) according to the invention and in particular from the particularly preferred compound of formula 1b.

Structurally similar compounds to the compounds according to the invention are the compounds of formulas 4a and 4b:

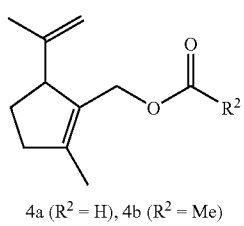

4a ($R^2$ = H), 4b ($R^2$ = Me)

These compounds of formulas 4a and 4b, however, have very clearly different odour or taste properties to the compounds according to the invention. The sensory properties of compounds 4a and 4b are described as follows:
4a: woody, patchouli-like (CH 579,015),
4b: ozonic, pungent (Zeszyty Naukowe-Politechnika Lodzka; Seria: Chemia Spozywcza (1980), 361 (35), 341-52).

Overall, it was therefore particularly surprising that each of the compounds according to the invention, in particular, however, the particularly preferred compound of formula 1b has a particularly strong fruity (apricot-like), floral (lilac), sweet and osmanthus-like odour or taste note.

The particular olfactory properties and the excellent substance properties, such as solubility in conventional cosmetic solvents, compatibility with further constituents of products of this type, etc., underline the particular suitability of the compounds according to the invention of formula (A) for the use purposes mentioned.

Corresponding aspects of the present invention relate to the use of a compound of formula (A), in particular in one of the configurations disclosed above as particularly preferred, as a fragrance and/or flavouring substance.

A use according to the invention of a compound of formula (A) as a fragrance and/or flavouring substance for imparting, modifying and/or reinforcing a fruity (in particular apricot), floral (in particular lilac), sweet and/or osmanthus-like odour or taste note is particularly preferred.

Fragrance substance compositions with a fruity, floral, sweet and osmanthus-like note are frequently looked for, in particular for the perfuming of surfactant-containing formulations, such as, for example, for shampoos, detergents or fabric softeners, and these should simultaneously have a pronounced blooming (odour from an aqueous surfactant-solution). The 2-alkoxymethyl-3-isoalkenyl-1-methylcyclopentenes according to the invention of formula (A) (in other words the formulas 1a, 1b, 2aE, 2aZ, 2bE, 2bZ) in a direct performance test with a comparative substance exhibit excellent properties and are therefore very suitable for "blooming" of surfactant solutions (see below for panel assessment). The present invention therefore also relates to the use of a compound of formula (A) for increasing the odour of other fragrance substances perceived above a surfactant-containing aqueous solution. That stated above applies here with respect to preferred configurations of the compound of formula (A).

The present invention, according to a further aspect, also relates to articles comprising one or more compounds of formula (A) as defined above. If an article according to the invention comprises only one compound of formula (A), in other words only one of the compounds 1a, 1b, 2aE, 2aZ, 2bE and 2bZ, the article also comprises another substance.

Preferred articles according to the invention comprise or consist, however, of two or more compounds of formula (A) as defined above.

In particular in the case of compounds of formula 2a and 2b, it is advantageous to use mixtures of the respective (E)- and (Z)-isomers. Accordingly, a preferred article according to the invention consists of a first and a second compound of formula (A) as defined above, R being identical in the first and the second compound, $R^1$ being methyl and the associated double bind of the first compound being (E)-configured and that of the second compound being (Z)-configured.

Particularly preferred articles according to the invention comprise a total quantity of compounds of formula (A) as defined above, which is sufficient to impart, to modify and/or to reinforce one, two, three or all the odour or taste notes from the group consisting of fruity (in particular apricot), floral (in particular lilac), sweet and osmanthus-like.

A particularly relevant aspect of the present invention relates to fragrance and flavouring substance compositions, which comprise one or more compounds of formula (A). Accordingly, a preferred article according to the invention is a fragrance or flavouring substance composition of this type, comprising one or more compounds of formula (A) as defined above as well as one or more further fragrance or flavouring substances. With regard to the preferred selection of the one or more further fragrance or flavouring substances, see below.

Preferred articles according to the invention frequently comprise a carrier or a substrate, which is in direct contact with the compound(s) according to the invention of formula (A) or the fragrance or flavouring substance composition according to the invention (as the preferred example of an article according to the invention).

A preferred fragrance or flavouring substance composition according to the invention comprises a total quantity of compounds of formula (A) as defined above in the range of 0.001 to 70% by weight, preferably 0.05 to 50% by weight and particularly preferably 0.5 to 25% by weight, based on the total quantity of the fragrance or flavouring substance composition.

With regard to the compounds of formula (A) to be preferably used in a fragrance or flavouring substance composition according to the invention, that which was stated above applies accordingly with regard to the preferred compounds of formula (A).

Of great interest for the composition work with regard to perfume are also fragrance substances, which themselves have a pronounced diffusivity (spatial effect) and/or improve the diffusivity of a perfume oil (fragrance substance compositions). The compounds according to the invention of formula (A), in other words the compounds of formula 1a, 1b, 2aE, 2aZ, 2bE and 2bZ exhibit these two effects.

The present invention also relates to a method for imparting, modifying and/or reinforcing an odour or taste, a quantity (a) of one or more compounds of formula (A), as defined above or (b) of a fragrance or flavouring substance composition according to the invention is brought into contact or mixed with a product.

It is obvious that a method according to the invention of this type will be used in particular for imparting, modifying and/or reinforcing an odour or taste with one, two, three or all the notes, fruity (in particular apricot), floral (in particular lilac), sweet and osmanthus-like.

A particularly preferred method according to the invention for modifying and/or reinforcing an odour or taste with one, two, three or all the notes, fruity (in particular apricot), floral (in particular lilac), sweet and osmanthus-like, comprises the following step:

mixing a quantity of one or more compounds of formula (A), as defined above (in particular according to one of the configurations described above as particularly preferred) comprising one or more other fragrance or flavouring substances with one, two, three or all the notes, fruity (in particular apricot), floral (in particular lilac), sweet and osmanthus-like, wherein the quantity used of the one or more compounds of formula (A) as defined above, is sufficient to sensorially modify and/or reinforce the odour or taste impression of the other fragrance or flavouring substances which cause one, two, three or all the notes, fruity (in particular apricot), floral (in particular lilac), sweet and osmanthus-like.

Completely in accordance, a method according to the invention for producing an article (according to the invention) comprises the following step:

mixing one or more compounds of formula (A) as defined above (preferably according to one of the configurations described above as particularly preferred) with further constituents, a quantity of one or more compounds of this type of formula (A) being used, which is sufficient to impart, to modify and/or to reinforce in the article an odour or taste note.

A fragrance or flavouring substance composition according to the invention (as an example of a preferred article according to the invention) is preferably produced in that one or more compounds of formula (A) as defined above is mixed with conventional further constituents of a fragrance or flavouring substance composition, the compounds according to the invention of formula (A) being used in a sensorially effective quantity, in other words in a quantity which is sufficient to impart, to modify and/or to reinforce an odour or taste note in the fragrance or flavouring substance composition. It is obvious that the quantity used is preferably sufficient (a) to convey or (b) to modify and/or reinforce (in comparison to a mixture of the other constituents) a fruity (in particular apricot), floral (in particular lilac), sweet and/or osmanthus-like odour or taste note in the fragrance or flavouring substance composition. Examples of conventional further constituents of fragrance or flavouring substance compositions are to be found below.

Further particularly preferred perfumed products according to the invention are therefore air and room fresheners, such as, for example room sprays, toilet fragrance blocks or air freshener gels.

Fruity (in particular apricot), floral (in particular lilac), sweet and osmanthus-like odour notes are used in diverse perfume compositions, for example in flower fragrance themes. The Example 1 following below of a "rose" fragrance theme (application in fabric softener) representatively demonstrates in a clear manner the olfactory effect of the compounds according to the invention using 2-ethoxymethyl-3-isopropenyl-1-methylcyclopentene 1b.

The compounds according to the invention of formula (A) can also be used to modify and/or reinforce the odour or taste of a fragrance or flavouring substance composition, in particular to provide a fragrance or flavouring substance composition with more freshness, fullness, radiation and/or roundness and/or to reinforce existing odour or taste notes of a fragrance or flavouring substance composition, in particular odour or taste notes of the tendencies to fruity (in particular apricot), floral (in particular lilac), sweet and osmanthus-like.

The present invention also relates to methods for producing a compound of formula (A) as defined above. In some investigations, various methods have been found to be advantageous, which in each case comprise the following steps:
(i) providing or producing a compound of formula (C) and
(ii) converting the compound of formula (C) in one or more steps, so that an allylic rearrangement and an etherification to the compound of formula (A) results.

In accordance with known methods, the production of the compounds according to the invention of formula (A) can be carried out in four steps for example proceeding from dehydrolinalool ($R^1$=H) or 3,7-dimethyl-6-nonen-1-in-3-ol ($R^1$=Me), compare the following reaction plan:

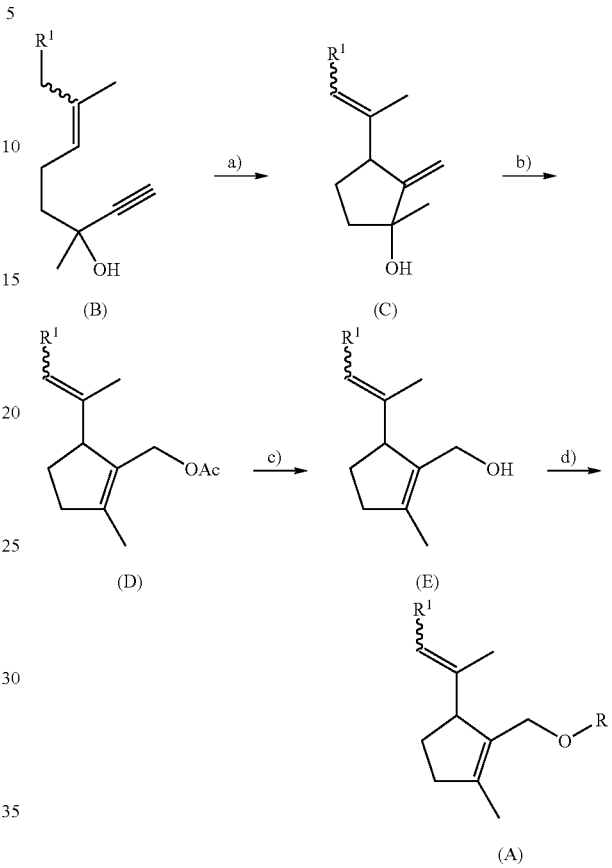

In each of the formulas represented in the above reaction plan, R and $R^1$ and the meandering line have a constant meaning, wherein with regard to the respective meaning, that stated above with regard to the compounds of formula (A) applies accordingly. In particular, therefore, the meandering line means, for example, that the associated double bond is (E)- or (Z)-configured if $R^1$=methyl.

Stage (step) a) is a thermal En reaction. This thermal En reaction takes place very selectively, for example by twelve hour heating of the pure substance at 185° C. In some investigations a yield of 99% was achieved here.

Stage (step) b) is an allylic rearrangement. The allylic rearrangement takes place regularly as a catalytic allyl rearrangement, tungstic acid preferably being used as the catalyst. In the course of allyl rearrangement, the product of stage a) is reacted for example with acetic acid anhydride, so the corresponding ethyl acetate is formed as the product of stage b). In our own investigations, a yield of 78% was achieved here with a reaction time of 2 hours and a reaction temperature of 135° C.

In stage (step) c), the ester formed is saponified to alcohol. This preferably takes place in that the ester is added dropwise into a solution of sodium methanolate in excess methanol and then stirred at ambient temperature. After two days of stirring, a yield of 90% was produced here in our own investigations.

In stage (step) d), the alcohol obtained in stage c) was etherified. This preferably takes place by the action of alkylation agents such as diethyl sulphate (DES) or dimethyl sulphate (DMS) with the addition of a phase transfer catalyst, to this extent tetrabutylammonium bromide, TBABr, can be used, for example. In this case, the alcohol is preferably presented in a mixture of sodium hydroxide solution (50%), toluene and phase transfer catalyst and DES or DMS are then added dropwise at about 50° C. To destroy the excess alkylation reagent, processing then takes place with concentrated ammonia solution. After the distillation, the ether can thus be isolated for example at a purity of 97% in about a 90% yield.

The four stage synthesis described above leads, with good yields, to the target product. However, it is disadvantageous that very many reaction steps have to be carried out and that toxicologically harmful materials are used in some reaction stages, such as, for example diethyl sulphate in stage d).

A new production method has therefore proven to be advantageous, which is not linked to previously known methods. By means of this new production method, the synthesis of the compounds according to the invention of formula (A) is successful in two steps and only harmless substances are used. The preferred two stage production method according to the invention is summarised in the following reaction plan:

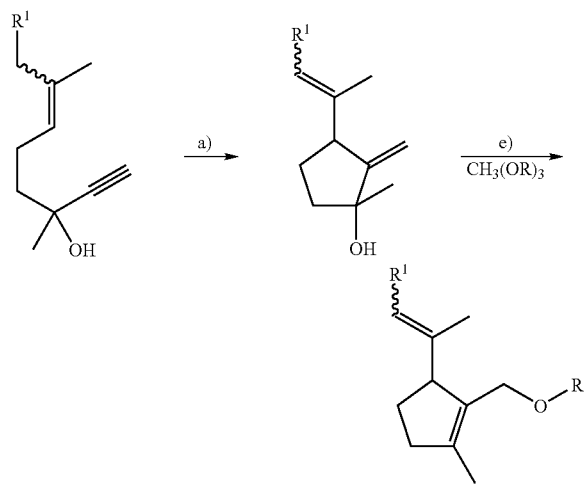

The groups R and $R^1$ again have a constant meaning in each formula shown. That which is stated above in each case applies accordingly. Stage (step) a) of the preferred production method according to the invention was carried out according to the four stage method described above. The reaction product of stage a) was then obtained—and this is where the relevant difference lies compared to the four stage method—by heating with reflux with the corresponding ortho ester. Ortho-formic acid trimethyl ester, ortho-formic acid triethyl ester, ortho-acetic acid trimethyl ester as well as ortho-acetic acid triethyl ester can be used in particular.

The En reaction according to stage a) is followed in this preferred method configuration according to the invention in the second stage e) by a combined allylic rearrangement and etherification to the desired compounds according to the invention of formula (A) in one step. A similar reaction was previously described only once in the literature although there a heterogeneous catalyst and so-called Baylis-Hillman adducts were worked with, which clearly differ from the present molecules according to the invention by the presence of a further electron-drawing group (Tetrahedron Lett. 2006, 47, 7619-7623).

In stage e) of the preferred production method according to the invention, in addition to the compounds according to the invention 2a and 2b, the weakly fragrant compounds 3a and 3b not according to the invention also occur and can be separated. Reference has already been made above to these compounds 3a and 3b. The separation preferably takes place when necessary by means of conventional separation methods such as distillation, for example.

Articles according to the invention may be configured as fragrance or flavouring substance compositions, fragrance or flavouring substance mixtures and perfume oils. Products of this type may be used in liquid form, undiluted or diluted with a solvent for perfuming. Suitable solvents are, for example, ethanol, isopropanol, diethyleneglycolmonoethylether, glycerol, propylene glycol, 1,2-butylene glycol, dipropylene glycol, diethyl phthalate, triethyl citrate, isopropyl myristate etc.

For many applications it is advantageous to use perfume oils containing compounds of formula (A) (fragrance substance mixtures; fragrance substance compositions) or flavouring substance compositions adsorbed on a carrier substance, which ensures both a fine distribution of the fragrance or flavouring substances in the product and a controlled release during application. Carriers of this type may be porous inorganic materials such as light sulphate, silica gels, zeolites, gypsums, clays, clay granulates, gas concrete etc. or organic materials such as woods, cellulose-based materials, sugar or plastics materials such as PVC, polyvinyl acetates or polyurethanes. This is a preferred configured of articles according to the invention, which, apart from one or more compounds of formula (A), comprise a carrier or a substrate, which is in direct contact with the compound(s) of formula (A) or the fragrance or flavouring substance composition, see above in this regard.

For other applications it is advantageous to use perfume oils containing compounds of formula (A) (fragrance substance mixtures; fragrance substance compositions) or flavouring substance compositions micro-encapsulated, spray dried, as an encapsulation complex or as an extrusion product and to add them in this form to the (pre)product to be perfumed or flavoured.

The properties of perfume oils modified in this manner are in many cases further optimised by so-called "coating" with suitable materials with regard to a more targeted fragrance release, for which purpose wax-like plastics materials, such as, for example, polyvinyl alcohol, are preferably used.

The micro-encapsulation of the fragrance or flavouring substance compositions according to the invention may take place, for example, by means of the so-called coacervation method with the aid of capsule materials for example made of polyurethane-like materials or soft gelatines. The spray-dried fragrance or flavouring substance compositions may be produced, for example, by means of spray drying of an emulsion containing the fragrance or flavouring substance composition, or dispersion, modified starches, proteins, dextrin and plant rubbers being able to be used as carrier substances. Encapsulation complexes may be produced, for example, by the introduction of dispersions of the fragrance or flavouring substance compositions and cyclodextrins or urea derivatives into a suitable solvent, for example water. Extrusion products may be implemented by melting the fragrance or flavouring substance compositions with a suitable wax-like material and by extrusion with subsequent solidification, optionally in a suitable solvent, for example isopropanol.

Perfume oils containing compounds of formula (A) (fragrance substance mixtures; fragrance substance compositions) or flavouring substance compositions may be used in concentrated form, in solutions or other modified form for the production of, for example, perfume extracts, eau de parfums, eau de toilettes, after-shaves, eau de cologne, pre-shave products, splash colognes and perfumed refresher tissues and the perfuming of acid, alkaline and neutral cleaning agents, such as, for example, floor cleaners, window glass cleaners, dishwasher detergents, bath and sanitary cleaners, scouring milk, solid and liquid WC cleaners, powdery and foam carpet cleaners. liquid washing agents, powder-like washing agents, pre-treatment washing agents such as bleaching agents, soaking agents and stain removers, laundry softeners, washing soaps, washing tablets, disinfectants, surface disinfection agents and air improvers in liquid, gel-like form or in a form applied to a solid carrier, aerosol sprays, waxes and polishes such as furniture polishes, floor waxes, shoe creams and body care agents, such as, for example, solid and liquid soaps, shower gels, shampoos, shaving soaps, shaving foams, bath oils, cosmetic emulsions of the oil-in-water, of the water-in-oil and of the water-in-oil-in-water type such as, for example, skin creams and lotions, face creams and lotions, sun protection creams and lotions, after sun creams and lotions, hand creams and lotions, foot creams and lotions, depilatory creams and lotions, after-shave creams and lotions, tanning creams and lotions, hair care products, such as, for example, hairsprays, hair gels, hair lotions, hair rinses, permanent and semi-permanent hair dyes, hair shaping means such as cold waves and hair smoothing agents, hair tonics, hair creams and lotions, deodorants and antiperspirants such as, for example, armpit sprays, roll-ons, deodorant sticks, deodorant creams or products of decorative cosmetics.

Additions with which one or more of the compounds according to the invention of formula (A) can be combined and with which they then together form an article according to the invention are, for example:

Preservatives, abrasives, anti-acne agents, agents against skin aging, antibacterial agents, anti-cellulitis agents, anti-dandruff agents, anti-inflammatories, irritation-preventing agents, irritation-inhibiting agents, antimicrobial agents, antioxidants, astringents, perspiration-inhibiting agents, antiseptic agents, antistatics, binders, buffers, carrier materials, chelating agents, cell stimulants, cleaning agents, care agents, depilatories, surface-active substances, deodorising agents, antiperspirants, softeners, emulsifiers, enzymes, essential oils, fibres, film formers, fixatives, foaming agents, foam stabilisers, substances for preventing foaming, foam boosters, fungicides, gelling agents, gel-forming means, hair care agents, hair shaping means, hair smoothing means, moisture-dispensing means, moisturising substances, moisture containing substances, bleaching agents, strengthening agents, stain-removing agents, optically brightening agents, impregnating agents, dirt-repelling agents, friction-reducing agents, lubricants, moisture creams, ointments, opacifiers, plasticising agents, covering means, polishes, brighteners, polymers, powders, proteins, lipid regulating agents, abrasive agents, silicones, skin soothing agents, skin cleaning agents, skin care agents, skin healing agents, skin brightening agents, skin protecting agents, skin softening agents, cooling agents, skin cooling agents, warming agents, skin warming agents, stabilisers, UV-absorbing agents, UV filters, washing agents, fabric softeners, suspended agents, skin tanning agents, thickening agents, vitamins, oils, waxes, fats, phospholipids, saturated fatty acids, singly or multiply unsaturated fatty acids, α-hydroxy acids, polyhydroxy fatty acids, liquifiers, dyes, colour-protecting agents, pigments, anti-corrosives, flavourings, taste substances, fragrance substances, polyols, surfactants, electrolytes, organic solvents or silicone derivatives.

The compounds according to the invention of formula (A) are primarily suitable for use in fragrance substance compositions (fragrance substance mixtures; perfume oils) or flavouring substance compositions because of their olfactory properties. The compositions according to the invention can in this case be used as a single substance or combined with a large number of further fragrance or flavouring substances in numerous products. The compounds can be particularly advantageously combined with other fragrance or flavouring substances in various different quantity ratios to form novel types of perfume compositions (as special fragrance substance mixtures) or flavouring substance compositions. Such fragrance or flavouring substance compositions preferably comprise two, three, four, five, six, seven, eight, nine, ten or more of the following mentioned extracts from natural raw materials and/or the following mentioned individual fragrance or flavouring substances.

Example of fragrance or flavouring substances with which the compounds according to the invention are advantageously combined to produce an article according to the invention, in particular to produce a fragrance or flavouring substance composition according to the invention are to be found, for example, in S. Arctander, Perfume and Flavor Chemicals, Vol. 1 and 11, Montclair, N.J., 1969, Selbstverlag or H. Surburg, J. Panten, Common Fragrance and Flavor Materials, 5$^{th}$ ed., Wiley-VCH, Weinheim 2006. Mentioned in detail are:

Extracts from natural raw materials such as natural oils, concretes, absolutes, resins, resinoids, balsams, tinctures such as, for example ambra tincture; amyris oil; angelica seed oil; angelica root oil; aniseed oil; valerian oil; basil oil; tree moss absolute; bay oil; mugwort oil; benzoin resin; bergamot oil; beeswax absolute; birch tar oil; bitter almond oil; savory oil; bucco leaf oil; cabreuva oil; cade oil; calamus oil; camphor oil; cananga oil; cardamom oil; cascarilla oil; cassia oil; cassie absolute; castoreum absolute; cedar leaf oil; cedar wood oil; cistus oil; citronella oil; lemon oil; copaiva balsam; copaiva balsam oil; coriander oil; costus root oil; cumin oil; cypress oil; davana oil; dill weed oil; dill seed oil; eau de brouts absolute; oak moss absolute; elemi oil; tarragon oil; eucalyptus-citriodora oil; eucalyptus oil; fenchel oil; spruce needle oil; galbanum oil; galbanum resin; geranium oil; grapefruit oil; guajak wood oil; gurjun balsam; gurjun balsam oil; helichrysum absolute; helichrysum oil; ginger oil; iris root absolute; iris root oil; jasmine absolute; calamus oil; camomile oil blue; camomile oil roman; carrot seed oil; cascarilla oil; pine needle oil; crisped mint oil; caraway oil; labdanum oil; labdanum absolute; labdanum resin; lavandin absolute; lavandin oil; lavender absolute; lavender oil; lemon grass oil; lovage oil; lime oil distilled; lime oil pressed; linaloe oil; litsea cubeba oil; laurel leaf oil; mace oil; marjoram oil; mandarin oil; massoi bark oil; mimosa absolute; musk grain oil; musk tincture; muscatel sage oil; nutmeg oil; myrrh absolute; myrrh oil; myrtle oil; clove leaf oil; clove blossom oil; neroli oil; olibanum absolute; olibanum oil; opopanax oil; orange blossom absolute; orange oil; oregano oil; palmarosa oil; patchouli oil; perilla oil; Peru balsam oil; parsley leaf oil; parsley seed oil; petitgrain oil; peppermint oil; pepper oil; pimento oil; pine oil; poley oil; rose absolute; rosewood oil; rose oil; rosemary oil; sage oil Dalmatian; sage oil Spanish; sandalwood oil; celery seed oil; spike lavender oil; star aniseed oil; styrax oil; marigold oil; fir needle oil; tea tree oil; turpentine oil; thyme oil; tolu balsam; tonka absolute; tuberoses absolute; vanilla extract; violet leaf absolute; verbena oil; vetiver oil; juniper berry oil; wine yeast oil; wormwood oil; wintergreen oil; ylang oil; ysop oil; civet absolute; cinnamon leaf oil; cinnamon bark oil and fractions thereof, or contents isolated therefrom;

individual fragrance substances from the group of hydrocarbons such as, for example 3-carene; α-pinene; β-pinene;

α-terpinene; γ-terpinene; p-cymol; bisabolene; camphene; caryophyllene; cedrene; farnesene; limonene; longifolene; myrcene; ocimene; valencene; (E,Z)-1,3,5-undecatriene; styrene; diphenylmethane;

aliphatic alcohols such as, for example hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-Pentamethyl-3/4-hepten-2-ol and 3,5,6,6-tetramethyl-4-methyleneheptane-2-ol; (E,Z)-2,6-nonadienol; 3,7-dimethyl-7-methoxyoctane-2-ol; 9-decenol; 10-undecenol; 4-methyl-3-decen-5-ol;

aliphatic aldehydes and acetiles thereof such as, for example hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanaldiethylacetal; 1,1-dimethoxy-2,2,5-trimethyl-4-hexene; citronellyloxyacetaldehyde; 1-(1-methoxy-propoxy)-(E/Z)-3-hexene;

aliphatic ketones and their oximes such as, for example 2-heptanone; 2-octanone; 3-octanone; 2-nonanone; 5-methyl-3-heptanone; 5-methyl-3-heptanonoxime; 2,4,4,7-tetramethyl-6-octen-3-one; 6-methyl-5-hepten-2-one;

aliphatic sulphur-containing compounds such as, for example 3-methylthio-hexanol; 3-methylthiohexylacetate; 3-mercaptohexanol; 3-mercaptohexylacetate; 3-mercaptohexylbutyrate; 3-acetylthiohexylacetate; 1-menthen-8-thiol;

aliphatic nitriles such as, for example 2-nonen acid nitrile; 2-undecanoic acid nitrile; 2-tridecanoic acid nitrile; 3,12-tridecadiene acid nitrile; 3,7-dimethyl-2,6-octadiene acid nitrile; 3,7-dimethyl-6-octenoic acid nitrile;

esters of aliphatic carboxylic acids such as, for example (E)- and (Z)-3-hexenylformate; ethylacetoacetate; isoamyl acetate; hexyl acetate; 3,5,5-trimethylhexylacetate; 3-methyl-2-butenylacetate; (E)-2-hexenylacetate; (E)- and (Z)-3-hexenylacetate; octylacetate; 3-octylacetate; 1-octen-3-ylacetate; ethylbutyrate; butylbutyrate; isoamylbutyrate; hexylbutyrate; (E)- and (Z)-3-hexenyl-isobutyrate; hexylcrotonate; ethylisovalerianate; ethyl-2-methylpentanoate; ethylhexanoate; allylhexanoate; ethylheptanoate; allylheptanoate; ethyloctanoate; ethyl-(E,Z)-2,4-decadienoate; methyl-2-octinate; methyl-2-noninate; allyl-2-isoamyloxyacetate; methyl-3,7-dimethyl-2,6-octadienoate; 4-methyl-2-pentylcrotonate;

acyclic terpene alcohols such as, for example citronellol; geraniol; nerol; linalool; lavadulol; nerolidol; farnesol; tetrahydrolinalool; tetrahydrogeraniol; 2,6-dimethyl-7-octen-2-ol; 2,6-dimethyloctane-2-ol; 2-methyl-6-methylene-7-octen-2-ol; 2,6-dimethyl-5,7-octadiene-2-ol; 2,6-dimethyl-3,5-octadiene-2-ol; 3,7-dimethyl-4,6-octadiene-3-ol; 3,7-dimethyl-1,5,7-octatriene-3-ol 2,6-dimethyl-2,5,7-octatriene-1-ol; as well as their formates, acetates, propionates, isobutyrates, butyrates, isovalerianates, pentanoates, hexanoates, crotonates, tiglinates and 3-methyl-2-butenoates;

acyclic terpene aldehydes and ketones such as, for example geranial; neral; citronellal; 7-hydroxy-3,7-dimethyloctanal; 7-methoxy-3,7-dimethyloctanal; 2,6,10-trimethyl-9-undecenal; geranylacetone; as well as the dimethyl- and diethylacetals of geranial, neral, 7-hydroxy-3,7-dimethyloctanal;

cyclic terpene alcohols such as, for example menthol; isopulegol; alpha-terpineol; terpineol-4; menthan-8-ol; menthan-1-ol; menthan-7-ol; borneol; isoborneol; linalooloxide; nopol; cedrol; ambrinol; vetiverol; guajol; as well as their formates, acetates, propionates, isobutyrates, butyrates, isovalerianates, pentanoates, hexanoates, crotonates, tiglinates and 3-methyl-2-butenoates;

cyclic terpene aldehydes and ketones such as, for example menthone; isomenthone; 8-mercaptomenthan-3-one; carvone; camphor; fenchone; alpha-Ionone; beta-Ionone; alpha-n-methylionone; beta-n-methylionone; alpha-isomethylionone; beta-isomethylionone; alpha-iron; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; 2-Methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedar wood oil (methylcedrylketone);

cyclic alcohols such as, for example 4-tert.-butylcyclohexanol; 3,3,5-trimethyl-cyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

cycloaliphatic alcohols such as, for example alpha,3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

cyclic and cycloaliphatic ethers such as, for example cineol; cedrylmethylether; cyclododecylmethylether; 1,1-dimethoxycyclododecan; (ethoxymethoxy)cyclodo-decan; alpha-cedrenepoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rosenoxide; 2-(2,4-dimethyl-3-cyclohexen-1-yl)-5-methyl-5-(1-methyl propyl)-1,3-dioxane;

cyclic and macrocyclic ketones such as, for example 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 7-cyclohexadecen-1-one; 8-cyclohexadecen-1-one; 9-cycloheptadecen-1-one; cyclopentadecanone; cyclohexadecanone;

cycloaliphatic aldehydes such as, for example 2,4-dimethyl-3-cyclohexencarbaldehyde; 2-methyl-4-(2,2,6-trimethyl-cyclohexen-1-yl)-2-butenal; 4-(4-hydroxy-4-methylpentyl)-3-cyclohexencarbaldehyde; 4-(4-methyl-3-penten-1-yl)-3-cyclohexencarbaldehyde;

cycloaliphatic ketones such as, for example 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphtalenylmethylketone; methyl-2,6,10-trimethyl-2,5,9-cyclododecatrienyl ketone; tert.-butyl-(2,4-dimethyl-3-cyclohexen-1-yl)ketone;

esters of cyclic alcohols such as, for example 2-tert-butylcyclohexylacetate; 4-tert-butylcyclohexylacetate; 2-tert-pentylcyclohexylacetate; 4-tert-pentylcyclohexyl acetate; 3,3,5-trimethyl cyclohexyl acetate; decahydro-2-naphthylacetate;

2-cyclopentylcyclopentylcrotonate; 3-pentyltetrahydro-2H-pyran-4-ylacetate; decahydro-2,5,5,8a-tetramethyl-2-naphthylacetate; 4,7-methano-3a,4,5,6,7,7a-hexahydro-5, or 6-indenylacetate; 4,7-methano-3a,4,5,6,7,7a-hexahydro-5, or 6-indenylpropionate; 4,7-methano-3a,4,5,6,7,7a-hexahydro-5, or 6-indenylisobutyrate; 4,7-methanooctahydro-5, or 6-indenylacetate;

esters of cycloaliphatic alcohol such as, for example 1-cyclohexylethylcrotonate;

esters of cycloaliphatic carboxylic acids such as, for example allyl-3-cyclohexylpropionate; allylcyclohexyloxyacetate; cis- and trans-methyldihydrojasmonate; cis- and trans-methyljasmonate; methyl-2-hexyl-3-oxocyclopentancarboxylate; ethyl-2-ethyl-6,6-dimethyl-2-cyclohexencarboxylate; ethyl-2,3,6,6-tetramethyl-2-cyclohexencarboxylate; ethyl-2-methyl-1,3-dioxolan-2-acetate;

araliphatic alcohol such as, for example benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenyl pentanol; 3-methyl-5-phenyl pentanol; 3-phenyl-2-propen-1-ol; 4-methoxybenzyl alcohol; 1-(4-isopropylphenyl)ethanol;

esters of araliphatic alcohols and aliphatic carboxylic acids such as, for example benzylacetate; benzylpropionate; benzylisobutyrate; benzylisovalerianate; 2-phenyl-ethylacetate; 2-phenylethylpropionate; 2-phenylethylisobutyrate; 2-phenyl-ethylisovalerianate; 1-phenylethylacetate; alpha-trichlormethylbenzylacetate; alpha,alpha-dimethylphenylethylacetate; alpha,alpha-dimethylphenylethylbutyrate; cinnamylacetate; 2-phenoxyethylisobutyrate; 4-methoxybenzylacetate;

araliphatic ethers such as, for example 2-phenylethylmethylether; 2-phenylethyliso-amylether; 2-phenylethyl-1-ethoxyethylether; phenylacetaldehyddimethylacetal; phenylacetaldehyde diethyl acetal; hydratropaaldehyde dimethyl acetal; phenylacetaldehyde glycerol acetal; 2,4,6-trimethyl-4-phenyl-1,3-dioxan; 4,4a,5,9b-tetra-hydroindeno[1,2-d]-m-dioxin; 4,4a,5,9b-tetrahydro-2,4-dimethylindeno[1,2-d]-m-dioxin;

aromatic and araliphatic aldehydes such as, for example benzaldehyde; phenylacetaldehyde; 3-phenylpropanal; hydratropaaldehyde; 4-methylbenzaldehyde; 4-methyl phenylacetaldehyde; 3-(4-ethylphenyl)-2,2-dimethylpropanal; 2-methyl-3-(4-isopropylphenyl)propanal; 2-methyl-3-(4-tert.-butylphenyl)propanal; 2-methyl-3-(4-isobutylphenyl)propanal; 3-(4-tert.-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylendioxybenzaldehyde; 3,4-dimethoxybenzaldehyde; 2-methyl-3-(4-methoxyphenyl)propanal; 2-methyl-3-(4-methylenedioxyphenyl)propanal;

aromatic and araliphatic ketones such as, for example acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanyl methyl ketone; 6-tert.-butyl-1,1-dimethyl-4-indanyl-methylketone; 1-[2,3-dihydro-1,1,2,6-tetramethyl-3-(1-methylethyl)-1H-5-indenyl]-ethanone; 5',6',7',8'-tetrahydro-3',5',5',6',8',8'-hexamethyl-2-acetonaphthone;

aromatic and araliphatic carboxylic acids and esters thereof such as, for example benzoic acid; phenyl acetic acid; methylbenzoate; ethylbenzoate; hexylbenzoate; benzyl-benzoate; methylphenylacetate; ethylphenylacetate; geranylphenylacetate; phenylethyl phenylacetate; methylcinnamate; ethylcinnamate; benzylcinnamate; phenylethylcinnamate; cinnamylcinnamate; allylphenoxyacetate; methylsalicylate; isoamylsalicylate; hexylsalicylate; cyclohexylsalicylate; cis-3-hexenylsalicylate; benzylsalicylate; phenylethylsalicylate; methyl-2,4-dihydroxy-3,6-dimethylbenzoate; ethyl-3-phenylglycidate; ethyl-3-methyl-3-phenylglycidate;

nitrogen-containing aromatic compounds such as, for example 2, 4,6-trinitro-1,3-dimethyl-5-tert.-butylbenzene; 3,5-dinitro-2,6-dimethyl-4-tert.-butylacetophenone; cinnamic acid nitrile; 3-methyl-5-phenyl-2-pentanoic acid nitrile; 3-methyl-5-phenylpentanoic acid nitrile; methylanthranilate; methyl-N-methylanthranilate; Schiff's bases of methylanthranilate with 7-hydroxy-3,7-dimethyloctanal, 2-methyl-3-(4-tert.-butylphenyl)propanal or 2,4-dimethyl-3-cyclohexencarbaldehyde; 6-isopropylchinoline; 6-isobutylchinoline; 6-sec.-butylchinoline; 2-(3-phenylpropyl)pyridine; indol; skatol; 2-methoxy-3-isopropyl pyrazine; 2-isobutyl-3-methoxypyrazine;

phenols, phenyl ethers and phenyl esters such as, for example estragol; anethol; eugenol; eugenylmethyl ether; isoeugenol; isoeugenylmethyl ether; thymol; carvacrol; diphenyl ether; beta-naphthylmethyl ether; beta-naphthylethyl ether; beta-naphthylisobutyl ether; 1,4-dimethoxybenene; eugenylacetate; 2-methoxy-4-methylphenol; 2-ethoxy-5-(1-propenyl) phenol; p-kresylphenylacetate;

heterocyclic compounds such as, for example 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

lactones such as, for example 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,12-dodecandioate; ethylene-1,13-tridecandioate; cumarin; 2,3-dihydrocumarin; octahydrocumarin.

The compounds according to the invention of formula (A) and their mixtures can be incorporated (in a sensorially effective quantity) in aromatised articles or articles to be aromatised, in particular preparations being used for food, mouth care or consumption. Particularly preferred preparations being used as food or for consumption are sweet and fruity applications and drinks.

Preparations being used as food or for consumption are, for example, baked goods (for example bread, dry biscuits, cakes, other pastries), confectionary (for example chocolates, bar chocolate products, other bar products, fruit gums, hard and soft caramels, chewing gum), alcoholic or non-alcoholic drinks (for example coffee, tea, wine, wine-containing drinks, beer, beer-containing drinks, liquors, schnapps, brandies, fruit-containing lemonades, isotonic drinks, refreshment drinks, nectars, fruit and vegetable juices, fruit or vegetable juice preparations), instant drinks (for example instant cocoa drinks, instant tea drinks, instant coffee drinks), meat products (for example ham, fresh sausage or raw sausage preparations, seasoned or marinated fresh or pickled meat products), eggs or egg products (dry egg, egg white, egg yolk), cereal products (for example breakfast cereals, muesli bars, pre-cooked ready rice products), milk products (for example milk drinks, milk ice cream, yoghurt, kefir, fresh cheese, soft cheese, hard cheese, dry milk powder, whey, butter, buttermilk, partially or fully hydrolysed milk protein-containing products), products made of soya protein or other soya bean fractions (for example soya milk and products manufactured therefrom, soya lecithin-containing preparations, fermented products such as tofu or tempe or products produced therefrom, soya sauces), fruit preparations (for example jams, fruit ice cream, fruit sauces, fruit fillings), vegetable preparations (for example ketchup, sauces, dried vegetables, deep frozen vegetables, pre-cooked vegetables, vegetables in vinegar, preserved vegetables), snacking articles (for example baked or fried potato crisps or potato dough products, bread dough products, extrudates based on maize or peanuts), products based on fat or oil or emulsions thereof (for example mayonnaise, salad cream, dressings, spice preparations), in particular ready dishes and soups (for example dry soups, instant soups, pre-cooked soups), spice, spice mixtures and in particular seasonings, which are used for example in the snack sector. After the incorporation of the compounds to be used according to the invention of formula (A) or mixtures, these preparations are preparations according to the invention.

Preparations according to the invention may be present, for example, as semi-ready products or as a spice mixture.

Preparations according to the invention may be used, in particular, as semi-ready products for producing further preparations being used for food or consumption, in particular in spray-dried form. Preparations according to the invention may also be present in the form of capsules, tablets (non-coated and coated tablets, for example gastric juice-resistant coatings) dragées, granulates, pellets, solid mixtures, dispersions in liquid phases, as emulsions, as powders, as solutions, as pastes or as other swallowable or chewable preparations as food supplements.

Preparations according to the invention being used for mouth care are, in particular, mouth and/or dental care agents, such as toothpastes, tooth gels, tooth powders, dental floss, toothpicks, mouth washes and chewing gums.

Further conventional active, basic, auxiliary and additional substances for preparations according to the invention being used for mouth care or consumption may be contained in quantities of 5 to 99.99% by weight, preferably 10 to 80% by weight, based on the total weight of the preparation. Furthermore, the preparations may have water in a quantity of up to 99.99% by weight, preferably 5 to 80% by weight, based on the total weight of the preparation.

The preparations according to the invention (as examples of articles according to the invention), containing one or more compounds of formula (A) or mixtures thereof, are produced according to a preferred configuration, in that the compounds or the compounds of formula (A) are incorporated as a substance, as a solution (for example in ethanol, water or 1,2-propylene glycol) or in the form of a mixture with a solid or a liquid carrier substance (for example maltodextrin, starch, silica gel) other flavourings or flavouring substances and optionally further auxiliary agents and/or stabilisers (for example natural or synthetic polysaccharides and/or plant gums such as modified starches or gum arabic) into a base preparation being used for food, mouth care or consumption. Advantageously, preparations according to the invention present as a solution and/or suspension or emulsion can also be converted by spray drying to a solid preparation according to the invention (semi-ready product).

The spray-dried solid preparations according to the invention (as an example of articles according to the invention) are, as semi-ready products, particularly well suited to the production of further preparations according to the invention. 50 to 95% by weight carrier substances, in particular maltodextrin and/or starch, 5 to 40% auxiliary substances, preferably natural or synthetic polysaccharides and/or plant gums such as modified starches or gum arabic are preferably contained in the spray-dried solid preparations according to the invention.

According to a further preferred embodiment, to produce the preparations according to the invention, the compound or the compounds of formula (A) and optionally other constituents of the preparation according to the invention are firstly incorporated in emulsions, in liposomes, for example proceeding from phosphatidycholin, in microspheres, in nanospheres or else in capsules, granulates or extrudates from a matrix suitable for food and items for consumption, for example made of starch, starch derivatives (for example modified starch), cellulose or cellulose derivatives (for example hydroxypropyl cellulose), other polysaccharides (for example dextrin, alginate, curdlan, carrageenan, chitin, chitosan, pullulan), natural fats, natural waxes (for example beeswax, carnauba wax), from proteins, for example gelatine or other natural products (for example shellack). In this case, depending on the matrix, the products can be obtained by spray drying, spray granulation, melt granulation, coacervation, coagulation, extrusion, melt extrusion, emulsion methods, coating or other suitable encapsulation methods and optionally a suitable combination of the aforementioned methods. In a further preferred production method for a preparation according to the invention, the compound or the compounds of formula (A) are firstly complexed with one or more suitable complexing agents, for example with cyclodextrins or cyclodextrin derivatives, preferably alpha- or beta-cyclodextrin and used in this complexed form.

A preparation according to the invention is particularly preferred in which the matrix is selected such that the compounds according to the invention of formula (A) are released in a delayed manner from the matrix so a long lasting effect is achieved. To this extent a fat, wax, polysaccharide or protein matrix is particularly preferred.

Further constituents which can be used for preparations according to the invention used as food or for consumption are conventional basic, auxiliary and additional substances for food and items for consumption, for example water, mixtures of fresh or processed, plant or animal basic or raw materials (for example raw, roast, dried, fermented, smoked and/or cooked meat, bones, cartilage, fish, vegetables, fruit, herbs, nuts, vegetables or fruit juices or pastes or mixtures thereof), digestible and non-digestible carbohydrates (for example saccharose, maltose, fructose, glucose, dextrins, amylose, amylopectin, inulin, xylane, cellulose, tagatose), sugar alcohols (for example sorbitol, erythritol), natural or hardened fats (for example suet, lard, palm oil, coconut oil, hardened plant oil), oils (for example sunflower oil, peanut oil, corn oil, olive oil, fish oil, soya oil, sesame oil), fatty acids or salts thereof (for example potassium stearate), proteinogenic or non-proteinogenic amino acids and related compounds (for example γ-aminobutyric acid, taurine), peptides (for example glutathione), native or processed proteins (for example gelatines), enzymes (for example peptidases), nucleic acids, nucleotides, taste corrigents for unpleasant taste impressions, further taste modulators for further taste impressions which are generally not unpleasant, other taste-modulated substances (for example inositol phosphate, nucleotides such as guanosine monophosphate, adenosine monophosphate or other substances such as sodium glutamate or 2-phenoxypropionic acid), emulsifiers (for example lecithins, diacylglycerols, gum Arabic), stabilisers (for example carrageenan, alginate), preservatives (for example benzoic acid, sorbic acid), anti-oxidants (for example tocopherol, ascorbic acid), chelating agents (for example citric acid), organic or inorganic acidification agents (for example malic acid, acetic acid, citric acid, tartaric acid, phosphoric acid), bitters (for example quinine, caffeine, limonin, amarogentin, humulones, lupulones, catechins, tannins) mineral salts (for example sodium chloride, potassium chloride, magnesium chloride, sodium phosphates), substances preventing enzymatic browning (for example sulphite, ascorbic acid), essential oils, plant extracts, natural or synthetic dyes or colour pigments (for example carotenoids, flavonoids, anthocyans, chlorophylls and derivatives thereof), spices, trigeminally acting substances or plant extracts, containing such trigeminally acting substances, synthetic, natural or flavouring substances that are identical to nature, or fragrance substances such as odour corrigents.

Dental care agents according to the invention (preparations being used as a basis for mouth care), which contain one or more compound(s) of formula (A) or a mixture of these compounds, generally comprise an abrasive system (abrading or polishing agent), such as, for example silicic acids, calcium carbonates, calcium phosphates, aluminium oxides and/or hydroxylapatites, surface-active substances such as, for example, sodium lauryl sulphate, sodium lauryl sarcosinate and/or cocamidopropyl betaine, moisture retaining agents such as, for example glycerol and/or sorbitol, thickeners such as, for example carboxymethylcellulose, polyethylene glycols, carrageenan and/or Laponite®, sweetening agents, such as, for example, saccharin, taste corrigents for unpleasant taste impressions, taste corrigents for further taste impressions which are generally not unpleasant, taste-modulated substances (for example inositol phosphate, nucleotides such as guanosine monophosphate, adenosine monophosphate and other materials such as sodium glutamate or 2-phenoxypropionic acid), active cooling ingredients such as, for example menthol, menthol derivatives (for example L-menthol, L-menthyl lactate, L-menthyl alkyl carbonates, menthone ketals, menthane carboxylic acid amides), 2,2,2-trialkyl acetic acid amides (for example 2,2-diisopropyl propionic acid methyl amide), icilin and icilin derivatives, stabilisers and active ingredients such as, for example sodium fluoride, sodium monofluorophosphate, tin difluoride, quaternary ammonium fluorides, zinc citrate, zinc sulphate, tin pyrophosphate, tin dichloride, mixtures of various pyrophosphates, triclosan, cetylpyridinium chloride, aluminium lactate, potassium citrate, potassium nitrate, potassium chloride, strontium chloride, hydrogen peroxide, flavourings and/or sodium bicarbonate or odour corrigents.

Chewing gums according to the invention (as further examples of preparations being used for mouth care) which contain one or more compounds of formula (A) or mixtures of these compounds generally combine a chewing gum base, i.e. a chewing mass becoming plastic on chewing, sugars of various types, sugar substitute substances, other sweet tasting substances, sugar alcohols, taste corrigents for unpleasant taste impressions, other taste modulators for further taste impressions which are generally not unpleasant, taste-modulated substances (for example inositol phosphate, nucleotides such as guanosine monophosphate, adenosine monophosphate or other substances such as sodium glutamate or 2-phenoxypropionic acid), moisture containing agents, thickeners, emulsifiers, flavourings and stabilisers or odour corrigents.

The invention will be described in more detail below with the aid of examples. If not otherwise stated all details relate to the weight.

The retention indices (RI) given below relate to the following GC conditions: column: 20 m DB wax, internal diameter 0.18 mm; film thickness df=0.18 μm; temperature programme 60-9-220° C., cold feed system (KAS).

EXAMPLE 1

Perfume Oil with or without
2-ethoxymethyl-3-isopropenyl-1-methylcyclopentene
(1b) ("Rose Perfume" Theme)

| Fragrance substance | A Weight parts | B Weight parts |
|---|---|---|
| undecanal (aldehyde C11) | 5.0 | 5.0 |
| benzophenone | 20.0 | 20.0 |
| citronellol | 110.0 | 110.0 |
| 1-cyclohexyl-ethyl-crotonate | 30.0 | 30.0 |
| decenol trans-9 | 5.0 | 5.0 |
| dihydromyrcenol | 40.0 | 40.0 |
| diphenyloxide | 10.0 | 10.0 |
| ethyl vanillin, 10% in DPG | 20.0 | 20.0 |
| eugenol | 10.0 | 10.0 |
| frambinon, 10% in DPG | 10.0 | 10.0 |
| geraniol | 60.0 | 60.0 |
| 15-pentadecenolide | 40.0 | 40.0 |
| 8-cyclohexadecenone | 40.0 | 40.0 |
| hexenylsalicylate cis-3 | 30.0 | 30.0 |
| ionone beta | 20.0 | 20.0 |
| 1-(2,4,4-trimethylcyclohex-2-en-1-yl)but-2-en-1-on-en-1-yl) | 5.0 | 5.0 |
| cyclohexadecanone | 20.0 | 20.0 |
| 4-tert.butyl-α-methyldihydrocinnamaldehyde | 80.0 | 80.0 |
| linalool | 80.0 | 80.0 |
| 2,2-dimethyl-3-(3-methylphenyl)-propanol | 20.0 | 20.0 |
| methylphenylacetate | 10.0 | 10.0 |
| palmarosa oil | 5.0 | 5.0 |
| phenoxyethyl alcohol | 30.0 | 30.0 |
| phenylethyl alcohol | 200.0 | 200.0 |
| tetrahydrolinalool | 40.0 | 40.0 |
| 2,4-dimethylcyclohex-3-en-1-carbaldehyde | 5.0 | 5.0 |
| 1,3-dimethyl-3-phenylbutylacetate | 5.0 | 5.0 |

-continued

| Fragrance substance | A Weight parts | B Weight parts |
|---|---|---|
| 1',1',5',5'-tetramethylhexahydro-spiro[1,3-dioxolan-2,8'(5'H)-2H-2,4a-methanonaphthalin | 5.0 | 5.0 |
| cinnamyl alcohol | 5.0 | 5.0 |
| dipropylene glycol | 40.0 | 10.0 |
| 2-ethoxymethyl-3-isopropenyl-1-methylcyclopentene (1b) | — | 30.0 |
| Total: | 1000.0 | 1000.0 |

DPG: dipropylene glycol

The two perfume oils A (not according to the invention) and B (according to the invention) were incorporated into a fabric softener and then assessed with respect to odour from the fabric softener (0.8% by weight dosage). The effect can be described in the opinion of the perfumers as follows: the perfume oil B according to the invention is fuller, rounder, fresher, more floral (in particular the notes lilac and osmanthus), fruitier (in particular apricot), damascon-like, rosier, more radiant.

EXAMPLE 2

View of the Compound of Formula (1b) (2-ethoxymethyl-3-isopropenyl-1-methylcyclopentene) in Four Stages Stage a):

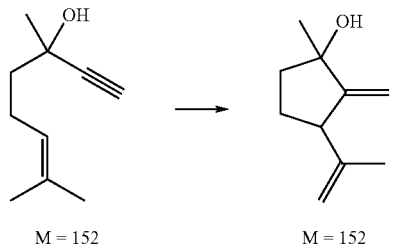

M = 152      M = 152

470 g (3.1 mol) dehydrolinalool (DHL) were heated at 185-192° C. with reflux. The reaction was followed by means of gas chromatography. It was heated until the remaining content of DHL (RI 1700) was about 1% (about 12-15 h). Cooling then took place. The crude yield was 464.9 g (98.9%), which contained the desired product in the form of two isomers in the ratio 56:44 (RI 1520 or 1580). This crude product was directly used in stage b).

Stage b):

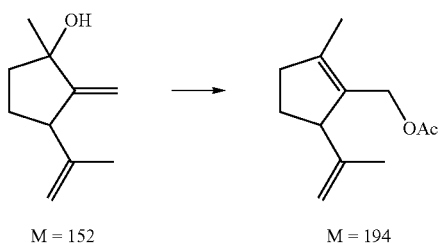

M = 152      M = 194

A mixture of 342.6 g acetanhydride, 0.3 g tungstic acid and 4.9 g sodium acetate were provided and heated to 135° C. At this temperature 464.9 g (3.06 mol) of crude product from stage a) were added dropwise within 30 min. and heated for 2 h with reflux. It was cooled to 80° C. and hydrolysed with 500 ml water. Extraction then took place twice each time with 300 ml hexane. The combined organic phases were then washed neutral one after the other with 200 ml water, 200 ml bicarbonate solution and again with 100 ml water. It was dried over sodium sulphate and the solvent removed on the rotary evaporator.

Crude yield: 579 g (97%).

Fractionation then took place in a vacuum on a 20 cm Vigreux column. Distillation conditions: 80-90° C./4 mbar yield: 341.3 g (78%). The GC purity of the desired product (RI 1658) was 96%, in addition 2% dehydrolinalyl acetate (RI 1685) were obtained.

Stage c):

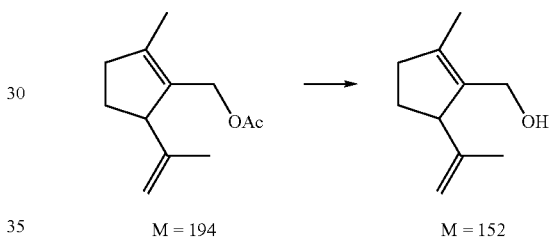

M = 194      M = 152

A mixture of 30 g Sodium methylate in 1000 ml methanol were provided. Within 15 min. 341 g of the acetate from stage b) were then added dropwise and allowed to stand for two days at ambient temperature (about 20° C.). The reaction was followed by gas chromatography. If educt-acetate is still present, heating briefly takes place. The methanol was then substantially removed on the rotary evaporator (40° C., 30 mbar) and the organic phase taken up with 500 ml methyl-tert.butyl ether (MTBE). Washing took place three times each with 300 ml water, drying took place over sodium sulphate and the solvent was removed on the rotary evaporator.

Crude yield: 268.9 g

Fractionation then took place on a 20 cm Vigreux column. Yield: 243.7 g (90%), distillation conditions: Kp=85° C./3 mbar GC purity: 96% alcohol, 2% dehydrolinalool Stage d):

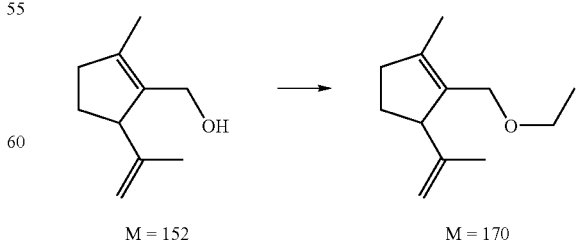

M = 152      M = 170

A mixture of 800 g NaOH 50%, 1600 ml toluene and 128.5 g tetrabutylammonium bromide (50% in water) was provided. At ambient temperature (about 20° C.) 243 g alcohol from stage c) were added and heated to 50° C. with vigorous stirring. 770 g diethyl sulphate were then added within 2.5 h. Stirring took place for 10 h at 50° C. For reaction control, samples were taken (destroy excess diethyl sulphate with ammonia). About 10% alcohol remained unreacted. 200 ml concentrated ammonia were then added dropwise and stirred for 4 h at 40° C. Cooling then takes place, the phases are separated and washed neutral with water. Evaporation to a low bulk then takes place at 40° C. and 30 mbar on the rotary evaporator.

Crude yield: 286.0 g

Fractionation then took place by means of a 20 cm Vigreux column.

Yield: 231.4 g (85%0, distillation conditions: 88-95° C./25 mm

All the fractions are put together with a content of ether >96%.

RI (compound 1b): 1390

RI (secondary product dehydrolinalylethyl ether): 1408 (~2-3%)

$^1$H-NMR (400 MHz, CDCl$_3$): δ=1.18 ppm (t), 1.60 (dd), 1.65 (m), 1.74 (m), 2.04 (m), 2.32 (m), 3.39 (dq), 3.46 (dq), 3.46 (m), 3.72 (d), 4.02 (d), 4.70 (m).

IR (Film): 890, 1100, 1370, 1450, 1650, 2850, 2950, 3000, 3180 cm$^{-1}$

MS (70 eV): 180, 165 (M-CH$_3$), 151 (M-C$_2$H$_5$), 136 (M-C$_2$H$_4$O), 134 (M-C$_2$H$_5$OH), 119 (100%, M-CH$_3$—C$_2$H$_5$OH), 91, 79, 41

EXAMPLE 3

Description of Compounds of Formula (A) in Two Stages

EXAMPLE 3.1

Description of the Compound of Formula 1b (2-ethoxymethyl-3-isopropenyl-1-methylcyclopentene)

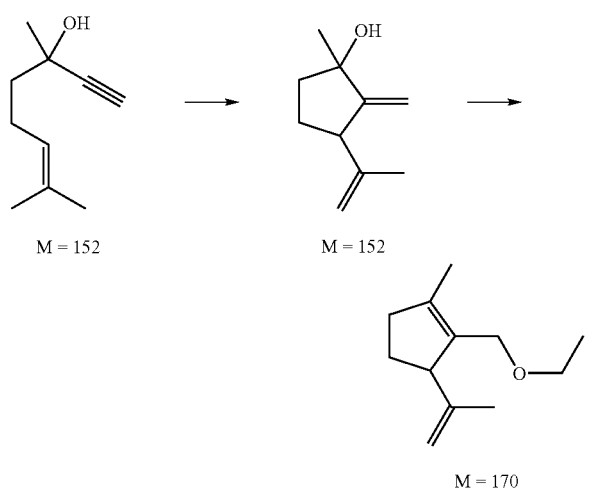

488 g dehydrolinalool were heated for 15 hours with reflux. Distillation off then took place at 3-4 mbar and at a bottom temperature of 120° C. from the residue, 488 g of distillate being obtained. 675 g of triethylorthoformate, 1380 g ethanol and 7.2 g p-toluene sulphonic acid were added to this and heated for 8 hours with reflux. After the end of the reaction, ethanol was distilled off and 500 g MTBE and water added in each case. After phase separation, the organic phase was washed neutral with water and the MTBE distilled off. The remaining residue was distilled at a jacket temperature of 110° C. and a vacuum of 1 mbar by means of a thin layer evaporator. 340 g distillate resulted which was then fractionated. 217 g of product (Kp$_{3mbar}$=62° C.) with a content of 98.7% was obtained. This corresponded to a yield of 40% of the theoretical yield.

EXAMPLE 3.2

Description of a Mixture of Compounds 2aE/2aZ or 2bE/2bZ

The (E)/(Z)-isomer mixtures 2aE/2aZ and 2bE/2bZ were produced analogously to Example 3.1. The (E)/(Z)-isomer ratio after distillation was in each case about 55:35.

The excellent application technology properties of 2-ethoxymethyl-3-isopropenyl-1-methylcyclopentene 1b will be made clear below with the aid of some examples.

EXAMPLE 4

Eau De Toilette (EDT)

EXAMPLE 5

Antiperspirant (AP) Stick

The imparting of a fruity, floral, osmanthus-like note in an eau de toilette (EDT) and in an antiperspirant (AP) stick was assessed in comparison to dimethyl benzyl carbonyl butyrate (DMBCB) (reference) by a panel on a scale of 0 (no note) to 6 (very strongly fruity, floral, osmanthus-like mote):

| EDT | 2-ethoxymethyl-3-isopropenyl-1-methylcyclopentene 1b | DMBCB |
|---|---|---|
| After 1 hour+ | 2.9 | 1.4 |
| After 3 hours+ | 2.1 | 0.9 |
| After 16 hours+ | 0.9 | 0.8 |

+time after applying a defined quantity on a paper fragrance strip

The EDT formulation consisted of 80% by weight ethanol, 19.7% by weight water and 0.3% by weight 2-ethoxymethyl-3-isopropenyl-1-methylcyclopentene 1b or DMBCB.

| AP stick | 2-ethoxymethyl-3-isopropenyl-1-methylcyclopentene 1b | DMBCB |
|---|---|---|
| From the stick | 2.4 | 1.9 |
| 1 hour after application to the skin | 2.8 | 1.1 |

The compound according to the invention accordingly proved to be superior.

EXAMPLE 6

Blooming

With regard to blooming (odour from an aqueous surfactant solution, here: aqueous solution of a fabric softener)

2-ethoxymethyl-3-isopropenyl-1-methylcyclopentene 1b was compared with DMBCB in a direct performance test (panel assessment 1-9):

| Blooming | 2-ethoxymethyl-3-isopropenyl-1-methylcyclopentene 1b | DMBCB |
|---|---|---|
| | 6 | 4 |

The compound according to the invention proved to be superior.

EXAMPLE 7

Diffusivity

Diffusivity is defined as the value of the odour perception in a specific time and at a specific distance. The higher the value the quicker and more strongly the substance is perceived.

The scale is defined by 1=no impact after 3 min. to 9=high impact after 10 sec.

Diffusivity is determined by smelling a certain quantity of a material in a Petri dish at a certain distance from the respective panelist. The dish is opened by a signal, the time stopped and the intensity assessed after the time of impact.

| Diffusivity | 2-ethoxymethyl-3-isopropenyl-1-methylcyclopentene 1b | DMBCB |
|---|---|---|
| | 5.9 | 3.8 |

The compound according to the invention proved to be superior.

EXAMPLE 8

Antiperspirant Stick

| Component | % by weight | % by weight |
|---|---|---|
| phenyl trimethicone (SilCare TM silicone 15 M 50) | 13.50 | 13.50 |
| cetearyl alcohol | to 100 | Ad 100 |
| Cetiol CC (dicaprylyl carbonate) | 13.50 | 13.50 |
| stearic acid | 3.50 | 3.50 |
| PEG-40 hydrogenated caster oil (Emulsogen TM HCO 040) | 4.10 | 4.10 |
| PEG-8 distearate (Cithrol 4 DS) | 4.10 | 4.10 |
| petrolatum | 6.90 | 6.90 |
| aluminium chlorohydrate | 14.00 | 13.80 |
| aluminium zirconium trichlorohydrex gly | 20.00 | 19.50 |
| 2,2-dimethyl-3-phenylpropanol (Muguet alcohol) | — | 0.25 |
| ethylhexylglycerol (octoxyglycerol) | — | 0.30 |
| 2-methyl-5-phenylpentan-1-ol (Rosaphen) | 0.30 | — |
| perfume oil B (according to the invention) from Example 1 | 0.80 | 1.00 |

EXAMPLE 9

Deodorant Sticks

| Component | A % by weight | B % by weight |
|---|---|---|
| sodium stearate | 7.00 | 8.00 |
| sodium palmitate | 1.00 | — |
| 1,2-propylene glycol | 42.00 | 45.00 |
| 1,2-butylene glycol | 3.00 | — |
| 2-methyl-5-phenylpentan-1-ol (Rosaphen) | 0.50 | 0.25 |
| 2-butyloctane acid | — | 0.50 |
| 2-hexyldecane acid | 0.10 | — |
| polyethylene glycol (25) cetearyl ether | 3.00 | 3.00 |
| ethanol | 20.00 | 20.00 |
| farnesol | — | 0.25 |
| Triclosan ® (5-chlor-2-(2,4-dichlorphenoxy)phenol) | 0.30 | — |
| parabenes (mixture of methyl-, ethyl-, propyl-, butyl-, isobutylparabene) | 0.30 | — |
| 1,2-hexanediol/1,2-octanediol (1:1) | — | 0.50 |
| 1,2-pentanediol | 0.50 | — |
| perfume oil B (according to the invention) from Example 1 | 1.00 | 0.90 |
| water | To 100 | To 100 |

EXAMPLE 10

Air Freshener in Gel Form 5 g Accurel (porous homo-polypropylene powder with 75% cavity proportion, a product from Akzo Nobel Faser AG, Obernburg, Germany) are loaded with 15 g perfume oil from Example 1 by mixing the two components under a vacuum. The resulting powder is then stirred at normal pressure with 4.5 g water (Mix 1). In another separate vessel, 2.5 g carrageen, 0.3 g chloroacetamide and 0.5 g calcium chloride dihydrate are dissolved in 62 g water with heating to about 75° C. Mix 1 was introduced into this solution while stirring and homogenised. The resulting still warm mixture is poured into the desired shape (spheres, hemispheres, cushions, cylinders, cuboids, cubes, shells or the like). After cooling to about 20° C., room fresheners in gel form are obtained, the loading of which with perfume oil is about 20% by weight.

EXAMPLE 11

Shampoo

Perfume oil compositions A and B from Example 1 were incorporated separately in a dosage of 0.2% by weight in each case into a shampoo basic mass with the following formulation:

| | |
|---|---|
| sodium lauryl ether sulphate (for example Texapon NSO, Cognis Germany GmbH) | 12% |
| cocamidopropyl betaine (for example Dehyton K, Cognis Germany GmbH) | 2% |
| sodium chloride | 1.4% |
| citric acid | 1.3% |
| phenoxyethanol, methyl-, ethyl-, butyl-, and propylparaben | 0.5% |
| peach fragrance substance mixture comprising gamma-undecalactone | 0.5% |
| water | 82.3% |

The pH of the shampoo basic mass was about 6. From this, 100 ml of 20% by weight aqueous shampoo solution was produced. Two strands of hair were washed together for 2 minutes in this shampoo solution and then rinsed under flowing hand-hot water for 20 seconds. One hair strand was wrapped wet in aluminium foil and the second hair strand was dried with a hairdryer. The two strands of hair were assessed with respect to odour by a panel. The shampoo and the hair strands with perfume oil B were described as fuller, rounder, fresher, more floral (in particular the lilac and osmanthus notes), fruitier (in particular apricot), more damascone-like, rosier, more radiant.

EXAMPLE 12

Fabric Softener

The perfume oil compositions A and B from Example 1 were in each case separately incorporated in a dosage of 0.7% by weight into a fabric softener basic mass with the following composition:

| | |
|---|---|
| quaternary ammonium methosulphate (Esterquat), about 90% (for example Rewoquat WE 18, Witco Surfactants GmbH) | 5.5% |
| alkyl dimethyl benzyl ammonium chloride, about 50% (for Preventol R50, Bayer) | 0.2% |
| Colour solution, about 1% | 0.3% |
| water | 94.0% |

The pH of the fabric softener basic mass was in the range of 2-3. Two material cloths were rinsed with 370 g of a 1% aqueous fabric softener solution in a line test machine in the softener programme for 30 minutes at 20° C. The cloths were wrung out and then spun for 20 seconds. One cloth was shrink-wrapped wet, and one was hung up to dry. The two cloths were then assessed with respect to odour by a panel. The cloth with perfume oil B was described as fuller, rounder, fresher, more floral (in particular the lilac and osmanthus notes), fruitier (in particular apricot), more damascone-like, rosier, more radiant.

EXAMPLE 13

Washing Powder 2-ethoxymethyl-3-isopropenyl-1-methylcyclopentene of formula 1b and perfume oil composition B from Example 1 were incorporated separately in a dosage of 0.3% by weight in each case into a washing powder basic mass with the following formulation:

| | |
|---|---|
| linear Na-alkyl benzyl sulfonate | 8.8% |
| ethoxylated fatty alcohol C12-18 (7 EO) | 4.7% |
| Na soap | 3.2% |
| defoamer DOW CORNING(R) 2-4248S POWDERED ANTIFOAM, silicone oil on zeolites as the carrier material | 3.9% |
| zeolite 4A | 28.4% |
| Na carbonate | 11.6% |
| Na salt of a copolymer of acrylic and maleic acid (Sokalan CP5) | 2.4% |
| Na silicate | 3.0% |
| carboxymethylcellulose | 1.2% |
| Dequest 2066 ([[(phosphonomethyl)imino]bis[(ethylennitrilo)bis (methylen)]]tetrakis-phosphonic acid, sodium salt) | 2.8% |
| visual brighteners | 0.2% |
| Na sulphate | 6.6% |
| protease | 0.4% |
| sodium perborate tetrahydrate | 21.8% |
| TAED | 1.0% |

Two material cloths were washed with 370 g of a 1% aqueous washing powder liquor (the pH value of the washing powder liquor is clearly in the alkaline range) in a line test in the machine main wash cycle for 45 minutes at 60° C. The cloths were firstly rinsed for 5 minutes in cold water, wrung out and then spun for 20 seconds. One cloth was shrink-wrapped wet and one hung out to dry.

EXAMPLE 14

Floral-Fresh Fruit Fragrance

| Constituent | Parts by weight |
|---|---|
| vanillin | 10.0 |
| ethyl acetate | 150.0 |
| ethyl butyrate | 200.0 |
| ethyl propionate | 50.0 |
| 2,6-nonadienol, 2% in Alcohol | 2.0 |
| cis-6-nonenal, 1% in Alcohol | 0.2 |
| methyl dihydrojasmonate | 7.0 |
| furaneol 15% in 1,2-propylene glycol | 30.0 |
| beta-Ionone | 0.2 |
| isoamyl acetate | 60.0 |
| isoamyl alcohol | 8.0 |
| isobutyl acetate | 100 |
| (2E,8Z)-undecadienic acid ethyl ester | 20 |
| (2E,6Z)-nonadienal, 1% in 1,2-propylene glycol | 2.0 |
| 6Z-nonenol | 2.0 |
| 2-ethoxymethyl-3-isopropenyl-1-methylcyclopentene of formula (1b) | 20 |
| 1,2-propylene glycol | 338.6 |

EXAMPLE 15

Carbonated Refreshment Drink

| Constituent | kg | Litre |
|---|---|---|
| Sugar syrup, 65% solid content | 153.850 | 116.55 |
| citric acid solution 50% | 3.000 | 2.460 |
| Flavouring from Example 14 | 0.200 | 0.250 |
| carbonated water | 880.740 | 880.740 |
| Total preparation | 1037.790 | 1000.000 |

SPECIFIC EMBODIMENTS

Specific embodiment one comprises a compound of formula (A)

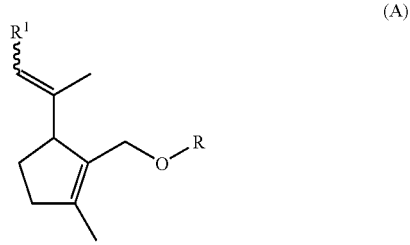

wherein, independently of one another, the following applies for groups R and $R^1$:
R is methyl or ethyl, and
$R^1$ is hydrogen or methyl, the meandering line indicating that for
$R^1$=methyl, the associated double bind is (E)- or (Z)-configured.

Specific embodiment two comprises the compound according to specific embodiment one, wherein the following applies:
R is ethyl
and
$R^1$ is hydrogen.

Specific embodiment three comprises a use of a compound as in specific embodiment one or two as a fragrance or flavouring substance.

Specific embodiment four comprises the use according to specific embodiment three for imparting, modifying and/or reinforcing a fruity (in particular apricot), floral (in particular lilac), sweet and osmanthus-like odour or taste note.

Specific embodiment five comprises a use of a compound as in specific embodiment one or two for increasing the odour of other fragrance substances perceived over a surfactant-containing aqueous solution.

Specific embodiment six comprises an article comprising one or more compounds of formula (A) as in specific embodiment one or two.

Specific embodiment seven comprises the article according to specific embodiment six, comprising or consisting of two or more compounds of formula (A) as in specific embodiment one or two.

Specific embodiment eight comprises the article according to specific embodiment six, comprising or consisting of a first and a second compound of formula (A) as in specific embodiment one, wherein in the first and the second compound R is identical, $R^1$ is methyl and the associated double bond of the first compound is (E)-configured and that of the second compound is (Z)-configured.

Specific embodiment nine comprises the article according to any one of specific embodiments six to eight, comprising a total quantity of compounds of formula (A) as in either of specific embodiment one or two, which is sufficient to impart, modify and/or reinforce one, two, three or all the odour and taste notes from the group consisting of fruity (in particular apricot), floral (in particular lilac), sweet and osmanthus-like.

Specific embodiment ten comprises the article according to any one of specific embodiments six to nine, wherein the article is a fragrance or flavouring substance composition, comprising one or more compounds of formula (A) as in either of specific embodiment one or two as well as one or more further fragrance or flavouring substances.

Specific embodiment eleven comprises the article according to any one of specific embodiments six to ten, further comprising a carrier or a substrate, which is in direct contact with the compound(s) of formula (A) or the fragrance or flavouring substance composition.

Specific embodiment twelve comprises the fragrance or flavouring substance composition according to either of specific embodiments ten or eleven, comprising a total quantity of compounds of formula (A) as in specific embodiments one or two in the range of 0.001 to 70% by weight, preferably 0.05 to 50% by weight and particularly preferably 0.5 to 25% by weight based on the total quantity of the fragrance or flavouring substance composition.

Specific embodiment thirteen comprises a method for imparting, modifying and/or reinforcing an odour or taste, wherein a quantity (a) of one or more compounds of formula (A) as in specific embodiment one or two or (b) of a fragrance or flavouring substance composition as in any one of specific embodiments ten to twelve is brought into contact or mixed with a product.

Specific embodiment fourteen comprises the method according to specific embodiment thirteen for imparting, modifying and/or reinforcing an odour or taste with one, two, three or all the notes, fruity (in particular apricot), floral (in particular lilac), sweet and osmanthus-like.

Specific embodiment fifteen comprises a method for modifying and/or reinforcing an odour or taste with one, two, three or all the notes, fruity (in particular apricot), floral (in particular lilac), sweet and osmanthus-like, comprising the following step:

mixing a quantity of one or more compounds of formula (A) as in specific embodiment one or two with one or more other fragrance or flavouring substances with one, two, three or all the notes, fruity (in particular apricot), floral (in particular lilac), sweet and osmanthus-like, wherein the quantity used of the one or more compounds of formula (A) as in specific embodiment one or two is sufficient to sensorially modify and/or reinforce the odour or taste impression of the other fragrance or flavouring substances, which cause one, two, three or all the notes, fruity (in particular apricot), floral (in particular lilac), sweet and osmanthus-like.

Specific embodiment sixteen comprises a method for producing a compound of formula (A) as in specific embodiment one or two comprising the following steps:

(i) providing or producing a compound of formula (C) and (ii) converting the compound of formula (C) in one or more steps, so that an allylic rearrangement and an etherification to from the compound of formula (A) results.

Specific embodiment seventeen comprises a method for producing an article as in any one of specific embodiments six to twelve, comprising the following step:

mixing one or more compounds of formula (A) as in specific embodiment one or two with further constituents, wherein a quantity of one or more compounds of formula (A) is used which is sufficient to impart, modify and/or reinforce in the article a fragrance or taste note.

It is claimed:

1. A compound of formula (A)

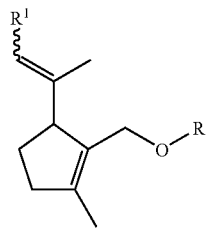

wherein:
R is methyl or ethyl;
R¹ is hydrogen or methyl; and the meandering line indicates that for
R¹=methyl, the associated double bond is (E)- or (Z)-configured.

2. The compound according to claim 1, wherein:
R is ethyl
and
R¹ is hydrogen.

3. A method of fragrancing or flavoring a substance comprising adding a compound as claimed in claim 1 to the substance.

4. The method according to claim 3 wherein a fruity, floral, sweet and osmanthus-like odor or taste note is imparted, modified and/or reinforced.

5. The method as claimed in claim 4 wherein the fruity odor or taste note is apricot.

6. The method as claimed in claim 4, wherein the floral odor or taste note is lilac.

7. An article comprising one or more compounds of formula (A) as claimed in claim 1.

8. The article according to claim 7, wherein the article comprises two or more compounds of formula (A).

9. The article according to claim 7, wherein the article consists of a first and a second compound of formula (A), wherein R in the first and the second compound are identical, R¹ is methyl, the associated double bond of the first compound is (E)-configured, and the associated double bond of the second compound is (Z)-configured.

10. The article according to claim 7, wherein the total quantity of compounds of formula (A), is sufficient to impart, modify and/or reinforce at least one of a fruity, floral, sweet or osmanthus-like odor or taste note.

11. The article according to claim 7, wherein the article is a fragrance or flavoring substance composition, comprising at least one compound of formula (A) as well as at least one further fragrance or flavoring substance.

12. The article according to claim 7, further comprising a carrier or a substrate in direct contact with the compound(s) of formula (A) or the fragrance or flavoring substance composition.

13. A method for producing an article as claimed in claim 7, comprising:

mixing one or more compounds of formula (A) with further constituents, wherein the quantity of one or more compounds of formula (A) is sufficient to impart, modify and/or reinforce a fragrance or taste note in the article.

14. A fragrance or flavoring substance composition comprising one or more compounds of formula (A) as claimed in claim 1, as well as one or more further fragrance or flavoring substances, wherein a total quantity of the compounds of formula (A) is in the range of 0.001 to 70% by weight based on the total quantity of the fragrance or flavoring substance composition.

15. The composition according to claim 14, wherein the total quantity of compounds of formula (A) is 0.05% to 50% by weight.

16. A method for imparting, modifying and/or reinforcing an odor or taste, comprising contacting or mixing a quantity (a) of at least one compound of formula (A) as claimed in claim 1 or (b) of a fragrance or flavoring substance composition, comprising at least one compound of formula (A) as claimed in claim 1 as well as at least one further fragrance or flavoring substance with a product.

17. The method according to claim 16, wherein the odor or taste is at least one fruity, floral, sweet and osmanthus-like note.

18. A method for modifying and/or reinforcing at least one of a fruity, floral, sweet or osmanthus-like odor or taste note, comprising:

mixing a quantity of at least one compound of formula (A) as claimed in claim 1 with at least one other fragrance or flavoring substance comprising at least one fruity, floral, sweet or osmanthus-like odor or taste note, wherein the quantity of the at least one compound of formula (A) is sufficient to sensorially modify and/or reinforce at least one of the fruity, floral, sweet or osmanthus-like odor or taste impression of the at least one other fragrance or flavoring substance.

19. A method for producing a compound of formula (A) as claimed in claim 1 comprising:
(i) providing or producing a compound of formula (C)

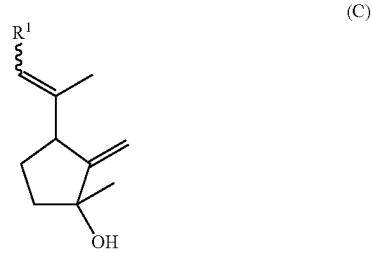

and
(ii) converting the compound of formula (C) to the compound of formula (A) through an allylic rearrangement and an etherification.

* * * * *